United States Patent
Kadir et al.

(10) Patent No.: US 8,150,112 B2
(45) Date of Patent: Apr. 3, 2012

(54) REGIONAL RECONSTRUCTION OF SPATIALLY DISTRIBUTED FUNCTIONS

(75) Inventors: Timor Kadir, Oxford (GB); David Schottlander, Sutton Courtenay (GB)

(73) Assignee: Siemens Medical Solutions USA, Inc., Malvern, PA (US)

(*) Notice: Subject to any disclaimer, the term of this patent is extended or adjusted under 35 U.S.C. 154(b) by 1164 days.

(21) Appl. No.: 11/892,658

(22) Filed: Aug. 24, 2007

(65) Prior Publication Data
US 2008/0056550 A1 Mar. 6, 2008

(30) Foreign Application Priority Data
Aug. 25, 2006 (GB) .................................. 0616859.5

(51) Int. Cl.
G06K 9/00 (2006.01)
(52) U.S. Cl. ................... 382/128; 382/131; 382/132
(58) Field of Classification Search ............... 382/128, 382/131, 132
See application file for complete search history.

(56) References Cited

U.S. PATENT DOCUMENTS

| | | | |
|---|---|---|---|
| 5,376,795 A | | 12/1994 | Hasegawa et al. |
| 5,638,817 A | * | 6/1997 | Morgan et al. ............... 600/425 |
| 6,016,439 A | * | 1/2000 | Acker ............................ 600/411 |
| 6,670,614 B1 | * | 12/2003 | Plut et al. ................. 250/363.04 |
| 6,740,883 B1 | * | 5/2004 | Stodilka et al. ......... 250/363.04 |
| 6,909,794 B2 | * | 6/2005 | Caspi ............................ 382/128 |
| 7,187,794 B2 | * | 3/2007 | Liang et al. .................... 382/131 |
| 7,231,076 B2 | * | 6/2007 | Fu et al. ........................ 382/131 |
| 2006/0233430 A1 | * | 10/2006 | Kimura ......................... 382/128 |
| 2006/0269130 A1 | * | 11/2006 | Maroy et al. ................... 382/173 |
| 2006/0285639 A1 | * | 12/2006 | Olivera et al. ................... 378/65 |
| 2007/0003123 A1 | * | 1/2007 | Fu et al. ........................ 382/131 |
| 2007/0191704 A1 | * | 8/2007 | DeCharms .................... 600/411 |
| 2007/0238986 A1 | * | 10/2007 | Graumann .................... 600/424 |

FOREIGN PATENT DOCUMENTS
EP 1 256 817 A1 11/2002

OTHER PUBLICATIONS

N.C. Hall, M.D., Ph.D et al. "Accurate SUV determination for small solitary pulmonary nodules using CT-based lesion volume estimates", IEEE, 2004, pp. 3426-3429.
G.J. Klein et al. "A Methodology for Specifying PET VOI's Using Multimodality Techniques", IEEE Transactions on Medical Imaging, vol. 16, No. 4, Aug. 1997, pp. 405-415.
British Search Report dated Dec. 20, 2006 (Two (2) Pages).

* cited by examiner

*Primary Examiner* — David A Vanore
(74) *Attorney, Agent, or Firm* — Crowell & Moring LLP (57) ABSTRACT

The invention addresses the problem of reproducibly estimating statistics in structurally significant regions of interest of medical volumes where the data is acquired as projections of a Cartesian-space distribution. The regions of interest (ROI) are specified to a high resolution using a spatial reference dataset, and these are mapped to the spatial frame of reference of the apparatus on which the data was acquired. This allows the regions to be projected on to the detector loci of the apparatus and ROI activity is estimated directly from measurement projections. The invention also addresses problems associated with poor delineation of ROIs.

16 Claims, 6 Drawing Sheets

Scenium Analysis

| Patients Name | |
|---|---|
| Patients | |
| Report Date | |
| Patient ID | |

| Region of Interest | Side | Min | Mean | Max | Min z-score | Z-score mean | Max z-score |
|---|---|---|---|---|---|---|---|
| Basal ganglia | L | 1.94 | 4.28 | 6.76 | -0.6 | 2.2 | 4.2 |
| Basal ganglia | R | 2.08 | 4,37 | 6.70 | -1.0 | 1.8 | 3.9 |
| Calcarine fissure and surrounding cortex | L | 1.41 | 4.55 | 6.54 | -2.3 | 0.4 | 4.0 |
| Calcarine fissure and surrounding cortex | R | 2.00 | 4.34 | 6.21 | -1.5 | -0.2 | 3.1 |
| Central region | L | 0.55 | 4.23 | 7.03 | -1.3 | 2.5 | 5.1 |
| Central region | R | 0.60 | 4.06 | 6.07 | -1.6 | 1.9 | 4.6 |
| Cerebellum | L | 0.89 | 3.60 | 5.29 | -5.3 | -0.7 | 4.4 |
| Cerebellum | R | 0.41 | 3.52 | 4.87 | -5.4 | 0.3 | 4.3 |
| Cingulate and paracingulate gyn | L | 2.17 | 4.80 | 6.83 | -0.4 | 4.7 | 7.0 |
| Cingulate and paracingulate gyn | R | 2.05 | 4.58 | 6.60 | 0.8 | 4.3 | 7.0 |
| Frontal lobe | L | 0.64 | 4.71 | 7.30 | -2.2 | 5.2 | 7.3 |
| Frontal lobe | R | 0.93 | 4.52 | 6.42 | -1.7 | 4.1 | 5.9 |
| Parietal lobe | L | 0.70 | 4.40 | 7.01 | -2.2 | 1.9 | 7.2 |
| Parietal lobe | R | 0.44 | 4.27 | 7.03 | -3.0 | 1.9 | 4.4 |
| Temporal lobe | L | 1.34 | 4.56 | 6.57 | -0.3 | 3.5 | 5.7 |
| Temporal lobe | R | 0.93 | 4.30 | 6.29 | -1.0 | 2.2 | 5.0 |

FIG 6

REGIONAL RECONSTRUCTION OF SPATIALLY DISTRIBUTED FUNCTIONS

The invention concerns the problem of reproducibly estimating statistics in structurally significant regions of interest of medical volumes where the data is acquired as projections of a Cartesian-space source distribution. It has utility in, for example, the estimation of tracer uptake in regions of interest of a body, following a medical scan such as Positron Emission Tomography (PET).

During a typical functional medical scanning process, a radioactive tracer is injected or otherwise ingested by a subject and after a suitable time, the tracer in the body of the subject is detected. The distribution of tracer throughout the body is mapped so that inferences can be drawn from the uptake of tracer in various regions of interest in the body.

In PET, a radiolabelled tracer such as [F-18]Fluoro-2-deoxy-glucose (FDG), an analogue of glucose which is used to study glucose metabolism, is injected in an object (e.g. a person). After a suitable time to allow for metabolism of the tracer a PET scan is performed in which measurements are made of radiation arising from radioactive decay of the radioactive label (the F-18) on the tracer.

In PET the radiation arises when positrons emitted by the radioactive label collide with an electron in a neighbouring atom. An annihilation reaction ensues in which two photons of gamma radiation are emitted at about 180° to each other.

The radiation detectors in the PET apparatus are arranged around the object so that the two photons arising from any radioactive decay event can be detected on a pair of detectors. It can then be inferred that the origin of the event lies along the line joining the detectors.

The foregoing description notwithstanding, it would be an over simplification to assume that the signal measured along any line through the object in a PET scan provides a direct measure of the radioactive tracer that is located along that line. There are two main reasons for this.

First, the radiation arising from a decay event is attenuated as it passes through the body, but the attenuation is not constant because different photons will pass through different tissue types and for different distances.

Second, the direction of the photons can be changed due to interactions with the environment (e.g. Compton scatter).

Nevertheless, it is true to say that the total (integral sum) of radiation detected along a line through a region of interest in the object is related to the uptake of tracer in that region. (A region of interest could be, for example, a particular organ where the object is a human or animal). By performing many such measurements along a large number of lines through the object it is possible to draw inferences, on a macroscopic level, about the distribution of tracer throughout the object.

Tomographic reconstruction provides estimates of values in a Cartesian co-ordinate system that are computed from projection data (the data acquired during the scan) in a radial co-ordinate system. An example of this is the inverse Radon Transform. Reconstruction is used widely in medical imaging for example for reconstruction of datasets acquired using Computed Tomography, Emission Tomography and Transmission Tomography equipment. Conventionally, the reconstruction provides an image in Cartesian space that is indexed by X,Y,Z co-ordinates. Individual volume elements (voxels) in the image are defined by a linear combination of basis functions of which the most common is the rectangular function. Other examples include points (comb function), B-splines etc. These are nearly always defined on an evenly spaced mesh covering the volume to be reconstructed. One exception to this is an approach to PET reconstruction in which the image is represented as a spatial spline-basis function, where the points are distributed unevenly with their density related to tracer activity density. In other approaches, anatomical prior information is used to derive a smoothing constraint on Maximum a Posteriori (MAP) reconstruction whereby edges are preserved in the PET image reconstruction in locations where there is an anatomical boundary.

Partial Volume Effect (PVE) in images that have been formed in this way leads to under or over estimation of radioactive concentrations in regional analysis of uptake. This can lead to errors in physiological interpretation from measurement data. PVE is due largely to inter-pixel correlations between neighbouring regions of differing uptake induced by reconstruction algorithms, partial pixel effects at region boundaries and discretization errors due to projection sampling over the pixel grid. By conventional methods, statistics such as mean and variance may be unreliable due to these factors as they may be under- or over-estimated. An example of where this is important is in weighted least squares fitting in compartment model analysis.

To counteract voxel-level bias due to PVE, regions of interest (ROI) are often used to calculate statistics as they cover a complete organ or a portion of an organ in which physiological and functional behavior is expected to be uniform. Often, the ROI is drawn on the image to follow the shape of the organ or the portion of the organ and this can often be done more accurately than the voxel level using visualization techniques such as image interpolation. However, reproducibility of region of interest delineation is poor since it is operator and image dependent, where the quality of the image is strongly related to the reconstruction method chosen. For instance variations in reconstruction parameters such as filter, iteration or smoothing strength can lead to variations in the final voxel values which leads to lack of trust in the quantification derived from the image by the clinician or researcher. To maximize region identification in the image, the operator frequently has to manipulate imaging display controls to maximize the distinguishibility of the regions using controls such as brightness and contrast, or window and level. This task leads to subjective variations between operators and significantly limits the repeatability of ROI delineation. Another feature that limits reproducibility includes the quality and calibration of the image display equipment which influences the number of grey levels observable by the operator.

Additionally, reconstruction of dynamic data on a voxel-wise basis has high computational demands and therefore for practical reasons, a smaller than optimal number of dynamic frames are conventionally reconstructed or sub-optimal reconstruction techniques are used. This can potentially lead to increased variance or reduced accuracy in quantitative analysis of the data.

In summary, all known PET reconstruction techniques reconstruct images of tracer distribution that introduce under- or over-estimation of tracer concentration estimates at a voxel-level and also in regions of interest mostly due to PVE and inaccuracy of ROI placement.

Conventional approaches to correcting for PVE account for partial volume elements by computing recovery coefficients, and account for correlations by deconvolution of a kernel that models the point spread function (PSF) of the system. The degree of sophistication of the required models increases as more tissue classes and complex reconstruction algorithms are used. An alternative approach [1] assumes a-priori knowledge of the ROIs, and reconstructs the mean activity for each ROI using conventional maximum likelihood expectation maximization ML-EM reconstruction. This technique was shown to provide significantly reduced bias in ROI values even for regions smaller than the intrinsic resolution limit of the scanner. In the context of this invention, we define "resolution" as the distance between two point sources below which they cannot be separated (i.e. they appear as a single merged point) in the image. We differentiate it from the pixel size which is also sometimes named "resolution". For sake of clarity, in this document, the pixel size will be referred to as "geometric sampling size". The advantage of this approach is that it is no longer necessary to model the reconstruction induced correlation, and projection discretization is modeled using the system matrix. However, the limitation of that work is that the ROIs were specified on a voxel-aligned grid and forward projected using a discrete system matrix, then back-projected using the same system matrix with ML-EM. Critically, use of a discrete system matrix such as this cannot recreate the partial pixel effect that is due to object size and boundary effect thereby ignoring one of the central contributory factors to PVE.

According to a first aspect of the invention, a method of estimating tracer uptake in a subject of a functional medical scan comprises the steps set out in claim 1 attached hereto.

According to a second aspect of the invention, apparatus for estimating tracer uptake in a subject of a functional medical scan comprises the features set out in claim 10 attached hereto.

The invention estimates region values for the entire imaged subject directly from projection data along with confidence values. It relies on knowing a-priori the structures for which values and confidence are required and these can be specified in continuous space (rather than discrete pixel space) or in sub-pixel space using any number of techniques. For the specific example of PET brain scans acquired using a combined MR-PET camera in which the MR data are intrinsically aligned with the PET data, it manifests as the reconstruction of quantities of tracer activity distribution and confidence values in all the regions of the brain without reconstructing any image of PET distribution.

This invention reduces the problem of partial volume effect by specifying the regions-of-interest (ROIs) to a geometric sampling size that is smaller than the intrinsic resolution of the scanning apparatus (e.g. continuously), computing a forward-backward projection matrix specifically for the regions and estimating the ROI activity directly from measurement projections. Studies show that PVE errors due to all three contributions listed previously are greatly reduced and that the quantitative uptake values have significantly less bias compared with conventional methods based on ROI analysis, reconstruction using regional filtered back projection (FBP-Huesman) or regional ML-EM (ML-ROI) using a voxel based system matrix.

This invention also addresses the problems associated with poor ROI delineation by reconstructing ROI statistics directly from the acquired projection data without the need for operator intervention. The ROIs can be defined, for instance, on a reference image matched to the geometry of the functional image. One example is the reconstruction of mean and variance of PET tracer distribution in brain regions in PET, for instance, using an intrinsically aligned segmented MRI or CT volume to define the regions of interest.

Finally, the invention represents a reduction in the computing capacity required when dynamic images are reconstructed on a voxel-wise basis. Consequently more time-frames can be analyzed routinely The invention will now be further described by non-limiting example, with reference to the following figures in which:

Figure 1:
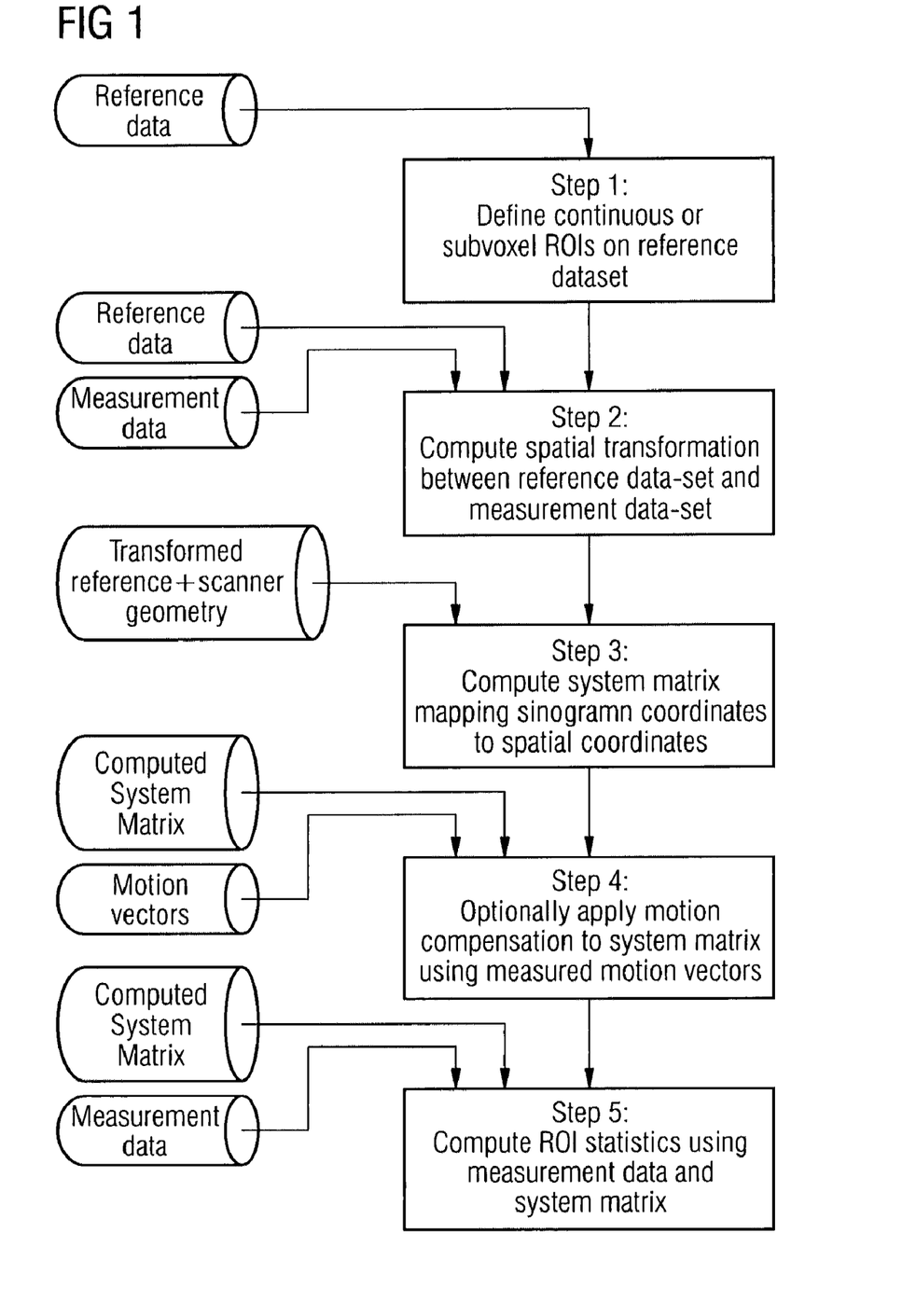
FIG. 1 is a flowchart illustrating the steps of the invention.

Referring to FIG. 1, in order to process a set of projection values in accordance with one embodiment of the invention, it is necessary first to define a set of ROIs from a reference data-set (step 1) that may be anatomical or functional (for instance grey matter, white matter and CSF, or according to a segmented brain template (as illustrated)). The ROIs are specified to a geometric sampling size that is smaller than the intrinsic resolution of the scanning apparatus.

Specification of the ROI's can be achieved by one of several methods including:

manual, semi-automatic or fully automatic segmentation derived from the functional image using amongst others: model based approaches, sub-pixel based approaches, statistical estimation approaches;

as per the previous paragraph but using an anatomical image or segmentation of regions using manual, semi-automatic or fully automatic rigid or deformable registration to an atlas, database, reference model or template.

At step 2, a transformation is computed and applied that positions and aligns the reference data-set into the image space coordinates of the measurement data.

In one example the measurement data is reconstructed once, then registered to the reference dataset to compute a transformation between the data-sets;

In another, it is ensured that the measurement data are intrinsically aligned with the reference data by using, for instance, a stereotactic frame or bed system to position the subject in the scanner in a position that is known relative to the reference data-set such that the transformation is known;

In yet another example, the reference data-set is acquired simultaneously with the acquisition of the measurement data such that intrinsic alignment is present, for example using a combined MR-PET, PET-Computerised Tomography (PET-CT) or Single Photon Emission Computed Tomography-CT (SPECT-CT) camera.

At step 3, a system matrix is calculated that projects the continuously specified or sub-voxel ROIs (in space and time) to discrete detector bins. The resulting system matrix represents the probability that an emission that originated from a particular ROI is detected in a particular detector pair (along a particular line of response).

Step 4 is an optional step which accounts for motion of the ROI during the acquisition. A time dependent geometric transformation matrix, that modifies the system matrix to account for detected motion in the ROIs of the imaged subject, is calculated and applied.

At step 5 a ROI value for tracer uptake along with a confidence level is calculated (for each ROI) as described below from the PET/SPECT acquired data. Calculation of the ROI values can be performed by applying the system matrix calculated in step 3 to the acquired data according to known methods. The back-projection can be performed by using the filtered back projection operation [2] with use of a system matrix or an iterative method. Estimating the reliability of the projected ROI values is done by summing over the variance of each projection involved in each ROI projected by the square projection operator.

The invention relies upon having accurately specified ROIs. An example of where this is the case is when MR and PET datasets are acquired simultaneously. In this case, no user intervention is required in order to define ROIs, eliminating uncertainty due to image quality, display equipment or user variability. Since no image is reconstructed, correlations between pixels are not relevant and therefore confidence estimates are easy to compute. The result is reconstruction of values and confidence estimates for all structural ROIs in the volume in a completely reproducible way.

Figure 2:
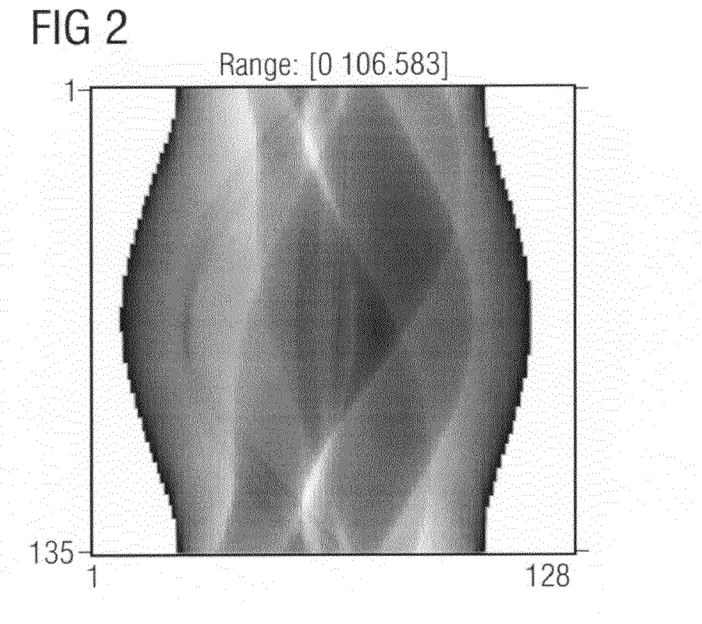
FIG. 2 shows an example of PET acquisition data displayed in sinogram format.

Referring to FIG. 2, each row represents a projection angle and the columns represent lines of response. Each pixel contains the total number of counts collected in a particular detector pair and so a complete column represents a complete projection.

Figure 3:
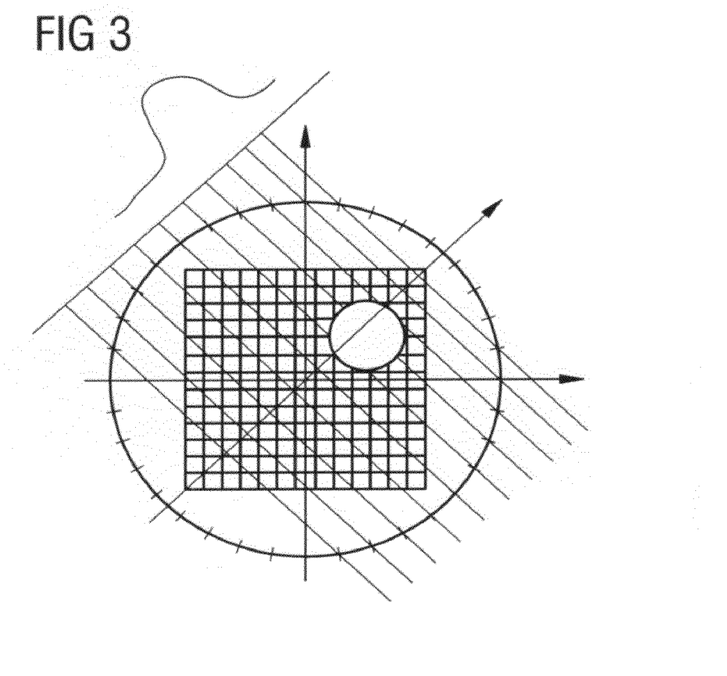
FIG. 3 shows a graphical representation of the projection at a single angle of an object in the field of the scan.

Referring to FIG. 3, the projection at a single angle of a spherical object corresponds to one column of the sinogram shown in FIG. 2.

Figure 4:
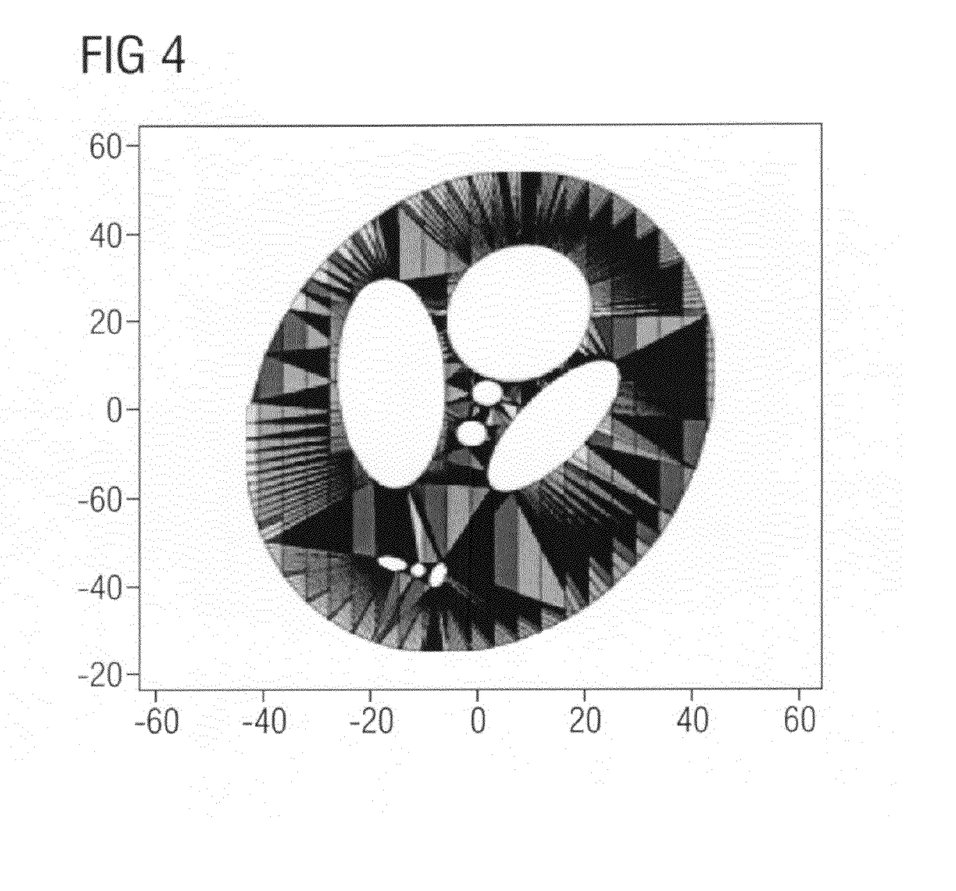
FIG. 4 shows an example of the computation of the probability that an emission from a background ROI is detected in a particular line of response at one particular projection angle (theta).

Referring to FIG. 4, the background region is triangulated and the area of the intersection of the triangles with each line of response is then computed. The total area within the region that intersects with the line of response from all triangles forms the required probability. This is repeated for all ROIs and all angles to complete the system matrix.

Figure 5A:
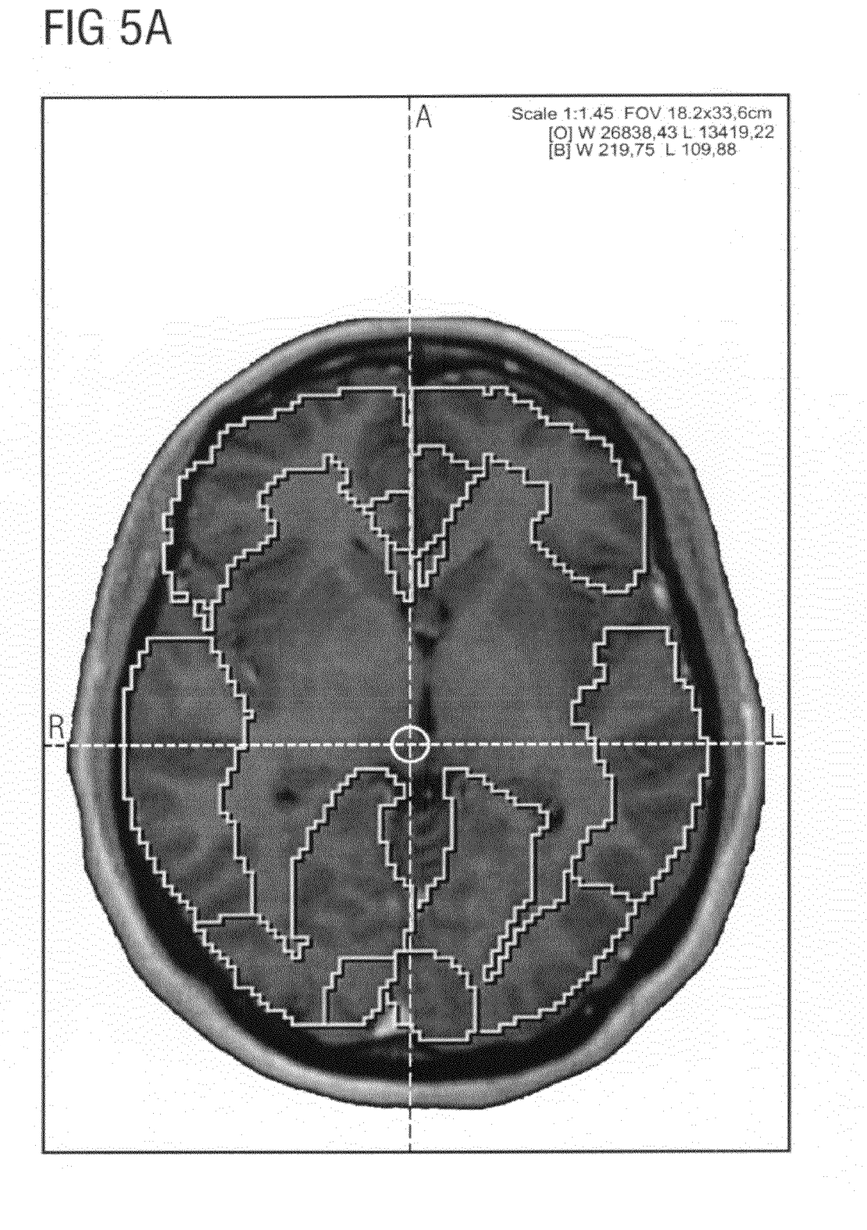
FIGS. 5*a* and 5*b* illustrate the use of the current invention to process the results of a combined PET-MRI scan and FIG. 6 illustrates schematically, an apparatus of the current invention.
Figure 5B:
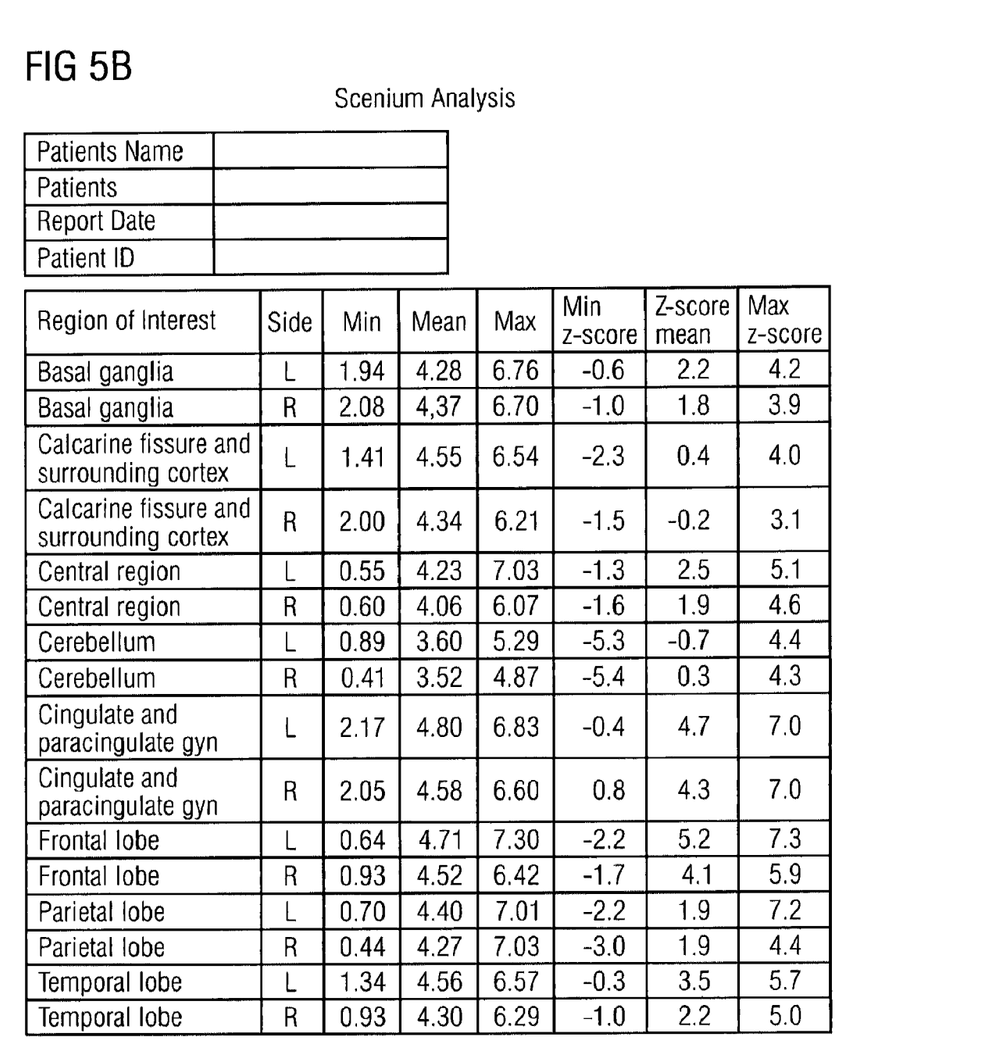

Referring to FIG. 5a, segmented MRI is intrinsically aligned with the PET data when data are acquired using a combined PET-MRI scanner. Referring to FIG. 5b, regional values and confidence values can be calculated directly without the need for reconstructing a PET image. The data so calculated can be compared against a database of normal values.

Figure 6:
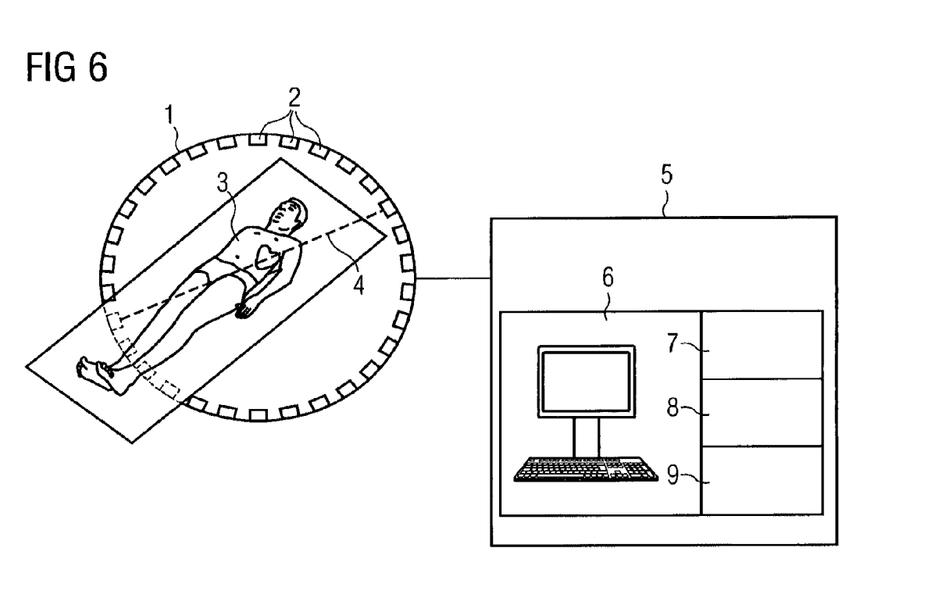

Referring to FIG. 6, apparatus for working the current invention comprises a scanner 1 having a plurality of detectors 2. The detectors are situated at loci which are known in relation to the position of the object 3 to be scanned.

In this embodiment, the scanner is a PET scanner wherein the detectors 2 are suitable for detecting radiation arising from the radioactive decay of a tracer injected onto the object (typically a person) 3. Simultaneous detection of a decay event by two detectors 2a, 2b allows an associated line 4 to be deduced, which passes through the object and projects on to said two detectors.

The apparatus further comprises a processing system 5 including a man-machine interface (MMI) 6 such as a display screen and keyboard/mouse, a processor 7 arranged to execute applications 8 (e.g. in response to commands received via MMI 6) and a repository 9 suitable for storing reference data such as a spatial reference dataset necessary for working the invention.

In the embodiment shown, the scanning apparatus 1 is directly linked to the processing system 5, providing a convenient route for data representing projection values measured by the scanner to be transferred to the processing system 5. This should not, however, be seen as limiting and in other embodiments the data could be transferred by any of a number of means including wireless connection, a network connection (e.g. the internet) or the data could be stored on a recording medium such as a CD-ROM for loading in the processing system.

Also, the repository 9 is shown as integral with the other components of the processing system as would be the case where the system were implemented as, for example, a personal computer with the reference data stored on the computer's memory. However, in another embodiment, the location of the repository could be remote from the other components of the processing system with data transfer again being facilitated by any of a number of known means.

During operation, emissions arising from radioactive decay of tracer in the object 3 is measured by detectors 2 to provide a set of projection values. Thus a set of values is obtained, each of which comprises the integral sum of a signal (gamma emission) measured along a line through the object which projects on to the locus of the detectors giving rise to that measurement. The signal so detected is related to the value of function of interest (in this case, uptake of tracer) in the ROI through which the line passes.

Through MMI 6, and with the aid of one or more of executable applications 8 a user is able to refer to a spatial reference dataset stored in repository 9 in order to specify regions of interest. The spatial reference dataset in this embodiment could comprise the results of one or more structural scans (e.g. MRI) of a similar (or the same) object. Alternatively, the spatial reference dataset could comprise the results of one or more functional medical scans such as PET.

Having specified the regions of interest, the user can then initiate one or more of executable applications 8 in order to map the spatial reference dataset on the spatial frame of reference on which the object and detectors were located during the measurement of the projection values. The regions of interest specified previously are then projected on to the loci of the detectors of the scanning apparatus and a value for tracer uptake (and an associated confidence value) is calculated for each region of interest.

REFERENCES

[1] R. E. Carson, "A maximum likelihood method for region-of-interest evaluation in emission tomography," *Journal of Computer Assisted Tomography*, vol. 10, pp. 654-63, 1986.

[2] R. H. Huesman, "A new fast algorithm for the evaluation of regions of interest and statistical uncertainty in computed tomography," *Physics in Medicine and Biology*, vol. 29, pp. 543-52, 1984.

The invention claimed is:

1. A method of estimating the value of a spatially distributed function in regions of interest in an object, from a set of projection values,
   said projection values comprising the integral sum of a signal detected along a line passing through a region of interest in the object, said signal being related to the value of the function in the region;
   the method comprising the steps of:
   measuring the set of projection values at a plurality of loci distributed about the object in a spatial frame of reference, each locus being a projection of one of said lines through the object;
   specifying a set of regions of interest (ROI's) from a spatial reference dataset, to a spatial geometric sampling size that is smaller than the resolution that is attainable by reconstruction of an image from the set of projection values;
   mapping the reference data set on the spatial frame of reference;
   projecting the regions of interest specified previously on to the loci and
   calculating a value, and an associated confidence measure, of the function for each ROI.

2. The method of claim 1 where the set of projection values is acquired as a functional or structural medical scan and the object is a living subject.

3. The method of claim 1 where the ROIs are defined by segmentation of a functional medical image scan.

4. The method of claim 3 and further including the step of registration of the functional or structural medical image scan to an atlas, database, reference model or template.

5. The method of claim 1, where the ROIs are defined by segmentation of a structural medical image scan.

6. The method of claim 1, where the mapping of the reference data set on the spatial frame of reference is achieved by reconstructing the set of projection values; registering the reconstructed dataset to the reference dataset and computing a transformation from one dataset to the other.

7. The method of claim 1, where the mapping of the reference data set on the spatial frame of reference is achieved by using a stereotactic frame or bed system to align the subject in a know position in relation to the reference data set such that a transformation from one dataset to the other can be inferred.

8. The method of claim 1, where the mapping of the reference data set on the spatial frame of reference is achieved by performing the functional medical scan and acquiring the reference dataset simultaneously.

9. The method of claim 1 and further including the step of calculating a time dependent geometric transformation matrix that modifies the system matrix to account for detected motion in the ROIs of the imaged subject.

10. Apparatus for estimating the value of spatially distributed functions in regions of interest in an object, comprising:
   a plurality of detectors, arranged at a plurality of loci distributed about the object in a spatial frame of reference to detect a signal along a plurality of lines through the object, said signal being related to the value of the function in the region of interest through which a line passes;
   a repository containing a spatial reference dataset suitable for defining regions of interest in articles such as the object;
   a man-machine interface which allows a person to input and receive information to and from the apparatus and
   a processor arranged to execute programmed applications which:
      specifies a set of regions of interest in the spatial reference dataset, to a spatial geometric sampling size that is smaller than the resolution that is attainable by reconstruction of an image from the set of projection values;
      map the spatial reference dataset on to the spatial frame of reference;
      project the regions of interest on to the loci of the detectors; and
      calculating a value, and an associated confidence measure, of the spatially distributed function for each region of interest.

11. The apparatus of claim 10, comprising a Positron Emission Tomography (PET) scanner and a computer arranged to execute the applications in response to user commands in order to estimate the uptake of a radiolabelled tracer in a human or animal body.

12. Apparatus according to claim 11, where the executable applications include means for reconstructing the set of projection values; registering the reconstructed dataset to the reference dataset and computing a transformation from one dataset to the other.

13. Apparatus according to claim 11, further comprising a stereotactic frame or bed system for aligning the object in a know position in relation to the reference data set such that a transformation from one dataset to the other can be inferred.

14. Apparatus according to claim 11, comprising a combined Positron Emission Tomography (PET) and Magnetic Resonance Imaging (MRI) scanner arranged to acquire the set of projection values as the results of a PET scan and the spatial reference dataset as the results of an MRI scan.

15. Apparatus according to claim 11, comprising a combined PET and Computed Tomography (CT) scanner arranged to acquire the set of projection values as the results of a PET scan and the spatial reference dataset as the results of a CT scan.

16. Apparatus according to claim 11, comprising a combined Single Photon Emission Computed Tomography (SPECT) and Computed Tomography (CT) scanner arranged to acquire the set of projection values as the results of a SPECT scan and the spatial reference dataset as the results of an CT scan.

* * * * *